United States Patent [19]

Denzel et al.

[11] 4,070,362
[45] Jan. 24, 1978

[54] AMINO DERIVATIVES OF TRIAZOLO(4,5-B)PYRIDINES

[75] Inventors: Theodor Denzel, Regensburg; Hans Hoehn, Tegernheim, both of Germany

[73] Assignee: E. R. Squibb & Sons, Inc., Princeton, N.J.

[21] Appl. No.: 444,203

[22] Filed: Feb. 21, 1974

[51] Int. Cl.$^2$ .......................................... C07D 471/04
[52] U.S. Cl. ..................... 260/295.5 B; 260/250 A; 260/256.4 N; 260/268 BC; 260/293.6; 260/294.8 C; 424/250; 424/251; 424/266; 424/267
[58] Field of Search ............ 260/295 F, 295.5 B, 260/293.6, 268 BC, 294.8 C, 256.4 N, 250 A

[56] References Cited
U.S. PATENT DOCUMENTS

| | | | |
|---|---|---|---|
| 3,828,057 | 8/1974 | Denzel et al. | 260/296 H |
| 3,929,812 | 12/1975 | Denzel et al. | 260/295.5 B |
| 3,971,800 | 7/1976 | Denzel et al. | 260/295.5 B |
| 3,971,801 | 7/1976 | Denzel et al. | 260/295.5 B |

OTHER PUBLICATIONS

Adrien et al., J. Chem. Soc., Perkin Trans 1(15), 1620–1624 (1973).

*Primary Examiner*—Alan L. Rotman
*Attorney, Agent, or Firm*—Lawrence S. Levinson; Merle J. Smith

[57] ABSTRACT

Amino derivatives of triazolo[4,5-b]pyridines having the general formula

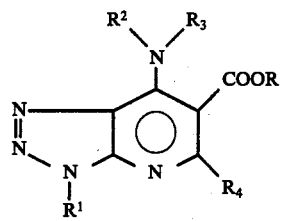

are disclosed. The novel compounds are useful as central nervous system depressants and antiinflammatory agents. In addition, the new compounds increase the intracellular concentration of adenosine 3',5'-cyclic monophosphate.

11 Claims, No Drawings

AMINO DERIVATIVES OF TRIAZOLO(4,5-B)PYRIDINES

SUMMARY OF THE INVENTION

This invention relates to new amino derivatives of triazolo[4,5-b]pyridines and salts of these compounds. These new compounds have the formula

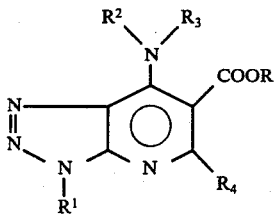

The symbols have the following meanings in formula I and throughout this specification.

R is hydrogen or lower alkyl. $R_1$ is hydrogen, lower alkyl, phenyl or phenyl-lower alkyl. The basic nitrogen group

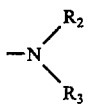

is an acyclic amino group, wherein $R_2$ and $R_3$ each is hydrogen, lower alkyl, lower alkenyl, lower alkanoyl, phenyl, substituted phenyl (i.e., the phenyl ring contains one or two simple substituents including lower alkyl, halogen, trifluoromethyl, amino, carboxy, preferably one of the last three substituents), phenyl-lower alkyl, di-lower alkylamino-lower alkyl, benzoyl, substituted benzoyl, phenyl-lower alkanoyl, substituted phenyl-lower alkanoyl, lower alkylsulfonyl, benzene-sulfonyl or substituted benzene-sulfonyl. The substituents in the phenyl groups are the same as described above (preferably only one of the last groups). This basic group may also form a heterocyclic of 5 or 6 members in which an additional nitrogen is present, i.e., the pyrrolidino, piperidino, pyrazolyl, pyrimidino, pyridazinyl or piperazino radicals, each of which may also bear as a substituent a hydroxy-lower alkyl group or one or two lower alkyl groups, especially the piperidine and piperazine heterocyclics. $R_4$ is hydrogen, lower alkyl or phenyl.

The lower alkyl groups in any of the foregoing radicals are straight or branched chain hydrocarbon groups of up to seven carbon atoms like methyl, ethyl, propyl, isopropyl and the like. The lower alkenyl groups are similar groups with one double bond. The lower alkanoyl groups include the acyl radical of the lower fatty acids having up to seven carbons, e.g., acetyl, propionyl, isopropionyl, butyryl and the like.

In each of the foregoing $C_1$ to $C_4$ members are preferred, especially the $C_1$ to $C_2$ members.

All four common halogens are contemplated, chlorine and bromine being preferred.

DETAILED DESCRIPTION OF THE INVENTION

Certain groups of compounds of formula I constitute preferred embodiments of the invention.

One group of preferred compounds of formula I includes those wherein R is hydrogen or lower alkyl, $R_1$ is hydrogen, lower alkyl, phenyl, benzyl or phenethyl, $R_2$ and $R_3$ each is hydrogen, lower alkyl, lower alkenyl (especially allyl), lower alkanoyl, $R_5$, $R_6$-phenyl, $R_5$, $R_6$-phenyl-lower alkyl, di-lower alkylamino-lower alkyl, $R_5$, $R_6$-benzoyl, methanesulfonyl, benzenesulfonyl or toluenesulfonyl, $R_4$ is hydrogen, $C_1$-$C_4$-lower alkyl or phenyl, $R_5$ is hydrogen, halogen, lower alkyl, trifluoromethyl, amino or carboxy, and $R_6$ is hydrogen, halogen or lower alkyl.

A preferred group of compounds includes those listed above but wherein $R_3$ is hydrogen only.

Another preferred group of compounds includes those listed in the second preceding paragraph above, but wherein the group

is pyrrolidino, piperidino, 4-lower alkylpiperidino (especially 4-methylpiperidino and 4-ethylpiperidino), pyrazolyl, pyrimidino, pyridazino, piperazino, or $N^4$-lower alkylpiperazino (especially $N^4$-methylpiperazino and $N^4$-ethylpiperazino). Especially preferred is the pyrrolidino series.

A particularly preferred group of compounds have the formula

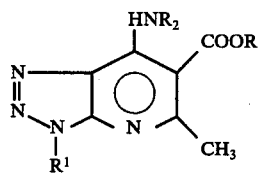

wherein R, $R_1$ and $R_2$ each is lower alkyl, preferably $C_1$ to $C_4$-lower alkyl and especially ethyl or butyl.

Salts of the above are also included.

The new compounds of formula I are formed by the following series of reactions. The symbols in the structural formulas have the same meaning as previously described.

A 2,4 dihydroxypyridine carboxylic acid ester of the formula

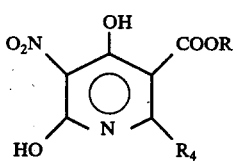

[produced analogous to the procedure described in Chem. Ber. 99, 244, (1966)] is made to react with an inorganic acid chloride like phosphorous oxychloride, producing a compound of the formula

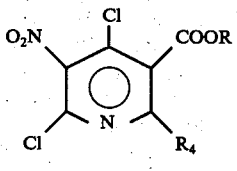

with two chlorine atoms in the 2 and 4 positions of the molecule. This compound is now treated in a solvent like alcohol with the appropriate amine of the formula

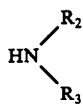 (V)

at about 80° C. in the presence of a base like triethylamine.

By this reaction a product of the formula

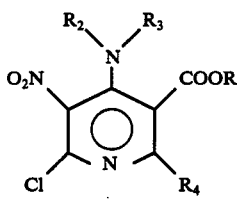 (VI)

is obtained.

Treatment of the compound of formula VI with an appropriate amine of the formula

 (VII)

in the presence of a base like triethylamine produces a compound of the formula

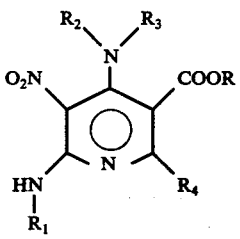 (VIII)

which is then hydrogenated catalytically with a catalyst like palladium or nickel or by reduction with a metal-acid pair like zinc in acetic acid, iron in hydrochloric acid or the like, producing a tri-amino compound of the formula

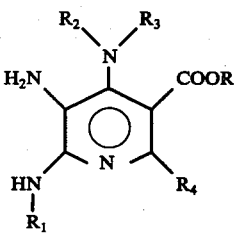 (IX)

A compound of formula I is obtained from the compound of formula IX by reaction of the latter with an alkali metal nitrite in an acid medium like sodium nitrite in acetic acid.

The compounds of formula I form salts which are also part of this invention. The salts include acid addition salts, particularly the non-toxic, physiologically acceptable members. The bases of formula I form salts by reaction with a variety of inorganic or organic acids providing acid addition salts including, for example, hydrohalides (especially hydrochloride and hydrobromide), sulfate, nitrate, borate, phosphate, oxalate, tartrate, malate, citrate, acetate, ascorbate, succinate, benzenesulfonate, methanesulfonate, cyclohexanesulfamate and toluenesulfonate. The acid addition salts frequently provide a convenient means for isolating the product, e.g., by forming and precipitating the salt in an appropriate menstruum in which the salt is insoluble, then after separation of the salt, neutralizing with a base such as barium hydroxide or sodium hydroxide, to obtain the free base of formula I. Other salts may then be formed from the free base by reaction with an equivalent of acid.

The new compounds of this invention are central nervous system depressants and may be used as tranquilizers or ataractic agents for the relief of anxiety and tension states, for example, in mice, cats, rats, dogs and other mammalian species, in the same manner as chlorodiazepoxide. For this purpose a compound or mixture of compounds of formula I, or non-toxic, physiologically acceptable acid addition salt thereof is administered orally or parenterally in a conventional dosage form such as tablet, capsule, injectable or the like. A single dose, or preferably 2 to 4 divided daily doses, provided on a basis of about 3 to 50 mg. per kilogram per day, preferably about 3 to 15 mg. per kilogram per day, is appropriate. These are conventionally formulated in an oral or parenteral dosage form by compounding about 10 to 250 mg. per unit of dosage with conventional vehicle, excipient, binder, preservative, stabilizer, flavor or the like as called for by accepted pharmaceutical practice.

The new compounds also increase the intracellular concentration of adenosine-3',5'-cyclic monophosphate, and thus by the administration of about 2 to 100 mg./kg./day, preferably about 10 to 50 mg./kg., in single or two to four divided doses in conventional oral or parenteral dosage forms such as those described above are used to alleviate the symptoms of asthma.

The new compounds of this invention, in addition, have antiinflammatory properties and are useful, for example, to reduce local inflammatory conditions such as those of an edematous mature or resulting from proliferation of connective tissue in various mammalian species such as rats, dogs and the like when given orally in dosages of about 5 to 50 mg./kg./day, preferably 5 to 25 mg./kg./day, in single or 2 to 4 divided doses, as indicated by the carageenan edema assay in rats. The active substance may be utilized in compositions such as tablets, capsules, solutions or suspensions containing up to about 300 mg. per unit of dosage of a compound or mixture of compounds of formula I or physiologically acceptable acid addition salt thereof. They may be compounded in conventional manner with a physiologically acceptable vehicle or carrier, excipient, binder, preservative, stabilizer, flavor, etc. as called for by accepted pharmaceutical practice. Topical preparations containing about 0.03 to 3 percent by weight of active substance in a lotion, salve or cream are also useful.

The following examples are illustrative of the invention. All temperatures are on the centigrade scale.

EXAMPLE 1

7-Butylamino-5-methyl-3-(2-methylpropyl)-[1,2,3]triazolo[4,5-b]pyridine-6-carboxylic acid ethyl ester a. 4,6-Dichloro-2-methyl-5-nitronicotinic acid ethyl ester 242 g. of 4,6-dihydroxy-2-methyl-5-nitronicotinic acid ethyl ester (1 mol.) is heated at 120° with 500 ml. of phosphorus oxychloride for 3 hours. After this time, the excess phosphorus oxychloride is removed in vacuo and the black residue decomposed by pouring into ice-water. About 1 liter of chloroform is added and the mixture is filtered from undissolved material. The organic layer is separated and the aqueous phase is extracted twice with 100 ml. portions of chloroform. The extract is dried over calcium chloride, filtered and evaporated to dryness. The resulting oil is crystallized with about 500 ml. of benzene, yielding 153 g. of 4,6-dichloro-2-methyl-5-nitronicotinic acid ethyl ester (55%), m.p. 45°-46°.

b. 4-Butylamino-6-chloro-2-methyl-5-nitronicotinic acid ethyl ester 139.5 g. of 4,6-dichloro-2-methyl-5-nitronicotinic acid ethyl ester (0.5 mol.) are dissolved in about 500 ml. of methanol. 60 g. of triethylamine are added and the solution is heated at reflux temperature. At this point 36.5 g. of n-butylamine are added dropwise. The solvent is then removed in vacuo and 500 ml. of benzene are added to the residue. The triethylamine hydrochloride is filtered off and the solvent evaporated. The resulting oil is dissolved in 300 ml. of methanol and yields on cooling 110 g. of 4-butylamino-6-chloro-2-methyl-5-nitronicotinic acid ethyl ester (70%), m.p. 35°-35° (methanol).

c. 4-Butylamino-6-(2-methylpropyl)amino-2-methyl-5-nitronicotinic acid ethyl ester 31.5 g. of butylamino-6-chloro-2-methyl-5-nitronicotinic acid ethyl ester (0.1 mol.) are dissolved in 150 ml. of methanol. At reflux temperature, a mixture of 11 g. of triethylamine and 7.3 g. of (2-methyl)propylamine are added. After the addition has been completed, heating is continued for an additional 30 minutes. The mixture is evaporated to dryness, about 100 ml. of water are added to the residue and the aqueous phase is extracted three times with 50 ml. portions of diethyl ether. The ether is dried with calcium chloride, filtered and the solvent distilled off. The yellow oily residue is crystallized with benzene and gives 31 g. of 4-butylamino-6-(2-methylpropyl)amino-2-methyl-5-nitronicotinic acid ethyl ester (88%) m.p. 26°-27° (benzene).

d. 5-Amino-4-butylamino-6-(2-methylpropyl)amino-2-methylnicotinic acid ethyl ester 17.6 g. of butylamino-6-(2-methylpropyl)amino-2-methyl-5-nitronicotinic acid ethyl ester (0.05 mol.) are dissolved in 100 ml. of butyl alcohol. 200 mg. of palladium on charcoal are added and the mixture is hydrogenated at 80° until the theoretical amount of hydrogen has been absorbed. The catalyst is filtered off and the mixture evaporated to dryness. The resulting oil, 5-amino-4-butylamino-6-(2-methylpropyl)amino-2-methylnicotinic acid ethyl ester, is used without further purification.

e. 7-Butylamino-5-methyl-3-(2-methylpropyl)[1,2,3]triazolo[4,5-b]pyridine-6-carboxylic acid ethyl ester 33 g. of the oil obtained in part d, 5-amino-4-butylamino-6-(2-methylpropyl)amino-2-methylnicotinic acid ethyl ester (about 0.1 mol.), are dissolved in 100 ml. of acetic acid 20 ml. of water. A solution of 0.75 g. of sodium nitrite in 20 ml. of water is added dropwise at about 10° with stirring. Stirring is continued for 10 hours. After this time, the mixture is evaporated. The resulting oil is mixed with 100 ml. of water and extracted three times with 50 ml. portions of ether. The ether phase is dried over sodium sulfate, filtered and evaporated. The residue, 7-butylamino-5-methyl-3-(2-methylpropyl) [1,2,3]triazolo[4,5-b]pyridine-6-carboxylic acid ethyl ester, is recrystallized from benzene, yield 27 g. (81%), m.p. 34°-36°.

EXAMPLE 2

7-Butylamino-5-methyl-3H-[1,2,3]triazolo[4,5-b]pyridine-6-carboxylic acid ethyl ester a. 6-Amino-4-butylamino-2-methyl-5-nitronicotinic acid ethyl ester 177.9 g. of 4-butylamino-6-chloro-2-methyl-5-nitronicotinic acid ethyl ester (0.5 mol.) obtained in Example 1b and 500 ml. of methanol are heated in an autoclave together with 300 ml. of aqueous ammonia (30%) at about 60° for 10 hours. After this time, the solvent is distilled off and the residual 6-amino-4-butylamino-2-methyl-5-nitronicotinic acid ethyl ester is recrystallized from methanol, yield 135g., m.p. 98-99°.

b. 5,6-Diamino-4-butylamino-2-methylnicotinic acid ethyl ester 29.6 g. of 6-amino-4-butylamino-2-methyl-5-nitronicotinic acid ethyl ester (0.1 mol.) are dissolved in 150 ml. of acetic acid. The solution is heated at reflux temperature. Zinc is added carefully until the mixture is colorless (about 20 g.). Heating is continued for an additional 10 minutes. The mixture is then evaporated to dryness and about 100 ml. of water are added. The solution is neutralized with dilute aqueous ammonia and extracted three times with 100 ml. portions of ether. The ether extracts are combined, dried with calcium chloride and the solvent evaporated. The oily residue. 5,6-diamino-4-butylamino-2-methylnicotinic acid ethyl ester, crystallizes from methanol, yield 21 g. (79%), m.p. 82°-83° methanol/$H_2O$).

c. 7-Butylamino-5-methyl-3H-[1,2,3]-triazolo[4,5-b]pyridine-6-carboxylic acid ethyl ester 2.66 g. of 5,6-diamino-4-butylamino-2-methylnicotinic acid ethyl ester (0.01 mol.) are dissolved in 20 ml. of acetic acid and 5 ml. of water. The mixture is cooled to 5° with stirring. At this temperature, a solution of 0.9 g. of sodium nitrite in 5 ml. of water is showly added dropwise. Stirring is continued for an additional 8 hours. The solvent is distilled off and the residue treated with 20 ml. of water and extracted three times with 10 ml. portions of chloroform. The organic layers are dried with sodium sulfate, filtered and evaporated. The crystalline 7-butylamino-5-methyl-3H-[1,2,3]-triazolo-[4,5-b]pyridine-6-carboxylic acid ethyl ester remains and is recrystallized from methanol, yield 2.3 g. (83%), m.p. 188°-189°.

EXAMPLE 3

7-(Ethylamino)-3-ethyl-5-methyl-3H-[1,2,3]-triazolo[4,5-b]pyridine-6-carboxylic acid ethyl ester a. 4,6-Di(ethylamino)-2-methyl-5-nitronicotinic acid ethyl ester 27.9 g. of 4,6-dichloro-2-methyl-5-nitronicotinic acid ethyl ester (0.1 mol.) obtained in Example 1a are dissolved in 200 ml. of methanol. The solution is heated at reflux temperature and a solution of 22.5 g. of ethylamine is added dropwise. After the addition is completed, the solvent is distilled off and the residue extracted with about 300 ml. of benzene. The benzene is removed and the residual 4,6-di(ethylamino)-2-methyl-5-nitronicotinic acid ethyl ester is recrystallized from methanol, yield 22.5 g. (76%), m.p. 63°–65°.

b. 5-Amino-4,6-di(ethylamino)-6-methylnicotinic acid ethyl ester 29.6 g. of 6-di(ethylamino)-2-methyl-5-nitronicotinic acid ethyl ester are dissolved in 100 ml. of butyl alcohol, 0.2 g. of palladium on charcoal (10%) are added and the solution is hydrogenated in an autoclave at 60° and 10 at. pressure. Filtration of the catalyst and evaporation of the solvent yields 26 g. of oily 5-amino-4,6-di(ethylamino)-6-methylnicotinic acid ethyl ester (98%).

c. 7-(Ethylamino)-3-ethyl-5-methyl-3H-[1,2,3]-triazolo[4,5-b]pyridine-6-carboxylic acid ethyl ester To a solution of 2.6 g. of 5-amino-4,6-diethylamino-6-methylnicotinic acid ethyl ester (0.01 mol.) in 20 ml. of acetic acid and 5 ml. water are added 0.8 g. of sodium nitrite in 5 ml. of water, dropwise, with stirring. The mixture is allowed to stand overnight. The solvent is distilled off and the residue extracted with 50 ml. of hot benzene. Filtration of the undissolved material and cooling yields 2 g. of 7-(ethylamino)-3-ethyl-5-methyl-3H-[1,2,3]-triazolo[4,5-b]pyridine-6-carboxylic acid ethyl ester (72%), m.p. 60°–61°.

EXAMPLE 4

7-Butylamino-3-ethyl-5-methyl-3H-[1,2,3]-triazolo[4,5-b]pyridine-6-carboxylic acid ethyl ester a. 4-Butylamino-6-ethylamino-2-methyl-5-nitronicotinic acid ethyl ester 4-Butylamino-6-chloro-2-methyl-5-nitronicotinic acid ethyl ester, obtained as in Example 1b, is treated with ethylamine according to the procedure of Example 1c. 4-Butylamino-6-ethylamino-2-methyl-5-nitronicotinic acid ethyl ester is obtained in 83% yield, m.p. 53°–55°.

b. 5-Amino-4-butylamino-6-ethylamino-2-methylnicotinic acid ethyl ester

Hydrogenation of 4-butylamino-6-ethylamino-2-methyl-5-nitronicotinic acid ethyl ester according to the procedure of Example 3b results in formation of oily 5-amino-4-butylamino-6-ethylamino-2-methylnicotinic acid ethyl ester, yield 94%.

c. 7-Butylamino-3-ethyl-5-methyl-3H-[1,2,3]-triazolo[4,5-b]pyridine-6-carboxylic acid ethyl ester 5-Amino-4-butylamino-6-ethylamino-2-methylnicotinic acid ethyl ester is treated with sodium nitrite following the procedure of Example 3c. 7-Butylamino-3-ethyl-5-methyl-3H-[1,2,3]-triazolo[4,5-b]pyridine-6-carboxylic acid ethyl ester is obtained, yield 73%, m.p. 42°–43°. Treatment with 2N hydrochloric acid in ethanol yields the hydrochloride salt.

The following additional compounds are produced by the procedure of Example 1 by utilizing the appropriately substituted nicotinic acid or amine:

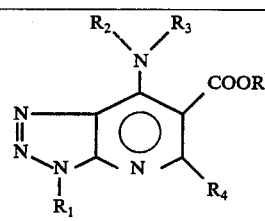

| Example | $R_1$ | $R_2$ | $R_3$ | $R_4$ | R |
|---|---|---|---|---|---|
| 5 | $CH_3-CH_2$ | $CH_3-CH_2$ | $CH_3-CH_2$ | $CH_3$ | $C_2H_5$ |
| 6 | $CH_3-CH_2$ | \multicolumn{2}{c}{$-CH_2-CH_2-N(CH_3)-CH_2-CH_2-$} | $CH_3$ | $C_2H_5$ |
| 7 | $CH_3-CH_2$ | $-(CH_2)_3N(C_2H_5)_2$ | H | $CH_3$ | $C_2H_5$ |
| 8 | $CH_3-CH_2$ | \multicolumn{2}{c}{$-CH_2-CH_2-NH-CH_2-CH_2-$} | H | $C_2H_5$ |
| 9 | $CH_3-CH_2$ | $CH_3-CH_2$ | $CH_3-CH_2$ | $CH_3-CH_2$ | $C_2H_5$ |
| 10 | $CH_3-CH_2$ | $-(CH_2)_2N(C_2H_5)_2$ | H | H | $C_2H_5$ |
| 11 | $CH_3-CH_2$ | H | H | $CH_3$ | $C_2H_5$ |
| 12 | H | \multicolumn{2}{c}{$-C(CH_3)=CH-C(CH_3)=N-$} | H | $C_2H_5$ |
| 13 | H | $C_3H_7$ | $C_3H_7$ | $CH_3$ | $C_2H_5$ |
| 14 | $CH_3-CH_2$ | \multicolumn{2}{c}{$-CH_2-CH_2-CH_2-CH_2-$} | $CH_3$ | $C_2H_5$ |
| 15 | $CH_3-CH_2$ | \multicolumn{2}{c}{$-CH_2-CH_2-N(CH_2-CH_2-OH)-CH_2-CH_2-$} | H | $C_2H_5$ |
| 16 | $CH_3-CH_2$ | H | H | H | H |
| 17 | $CH_3$ | $-(CH_2)_3CH_3$ | H | H | $C_2H_5$ |
| 18 | $CH_3$ | $-(CH_2)_3CH_3$ | H | H | H |
| 19 | $CH_3-CH_2$ | $-(CH_2)_3CH_3$ | H | H | H |
| 20 | $CH_3-CH_2$ | \multicolumn{2}{c}{$=CH-C(CH_3)=C(CH_3)-C=N$} | H | $C_2H_5$ |

-continued

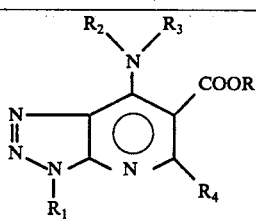

| Example | R₁ | R₂ | R₃ | R₄ | R |
|---|---|---|---|---|---|
| 21 | —CH₂—C₆H₅ | —(CH₂)₃CH₃ | H | H | $C_2H_5$ |
| 22 | $CH_3—CH_2$ | 3-CF₃-C₆H₄— | H | $CH_3$ | $C_2H_5$ |
| 23 | $CH_3—CH_2$ | 3-CF₃-C₆H₄— | H | H | H |
| 24 | $CH_3—CH_2$ | —CH₂—CH(CH₃)₂ | H | H | $C_2H_5$ |
| 25 | $CH_3—CH_2$ | —CH(CH₃)CH₂CH₃ | H | H | $C_2H_5$ |
| 26 | H | —CH₂—C₆H₅ | H | H | $C_2H_5$ |
| 27 | $CH_3—CH_2$ | —CH₂—CH₂—C₆H₅ | H | H | $C_2H_5$ |
| 28 | $CH_3—CH_2$ | —(CH₂)₃CH₃ | H | $CH_3$ | $C_2H_5$ |
| 29 | $CH_3—CH_2$ | —(CH₂)₂CH₃ | H | H | $C_2H_5$ |
| 30 | —CH₂—CH₂—C₆H₅ | —CH(CH₃)₂ | H | H | $C_2H_5$ |
| 31 | $CH_3—CH_2$ | —(CH₂)₅CH₃ | H | H | $C_2H_5$ |
| 32 | $CH_3—CH_2$ | —(CH₂)₃CH₃ | H | $CH_3$ | H |
| 33 | H | —C(CH₃)₃ | H | H | $C_2H_5$ |
| 34 | $CH_3—(CH_2)_3—$ | —(CH₂)₃CH₃ | H | H | $C_2H_5$ |
| 35 | $CH_3—CH_2$ | 2,6-(CH₃)₂-C₆H₃— | H | H | $C_2H_5$ |
| 36 | H | 2,6-(CH₃)₂-C₆H₃— | H | $CH_3$ | H |
| 37 | $CH_3—CH_2$ | 2-COOH-C₆H₄— | H | H | $C_2H_5$ |
| 38 | $CH_3(CH_2)_3—$ | —(CH₂)₃CH₃ | H | $CH_3$ | $C_2H_5$ |
| 39 | C₆H₅— | —(CH₂)₃CH₃ | H | H | $C_2H_5$ |
| 40 | $CH_3—CH_2—$ | $CH_3SO_2—$ | $CH_3—$ | H | $CH_3—CH_2—$ |
| 41 | $CH_3—CH_2—$ | 4-Cl-C₆H₄-CO— | H | H | $CH_3—CH_2—$ |
| 42 | $CH_3—CH_2—$ | 4-Cl-C₆H₄-CO— | $CH_3—(CH_2)_3—$ | H | $CH_3—CH_2—$ |
| 43 | $CH_3—CH_2—$ | 4-CH₃-C₆H₄-SO₂— | $Na^+$ | $CH_3$ | $CH_3—CH_2—$ |
| 44 | $CH_3—CH_2—$ | CH₂=CH—CH₂— | H | H | $CH_3—CH_2$ |
| 45 | $CH_3—CH_2—$ | 2-NH₂-C₆H₄— | H | H | $CH_3—CH_2—$ |
| 46 | $CH_3—CH_2—$ | C₆H₅-CH₂CO— | H | H | $CH_3—(CH_2)_5$ |
| 47 | $CH_3—CH_2—CH_2—$ | $CH_3—(CH_2)_3—$ | H | H | $CH_3—CH_2$ |
| 48 | $CH_3—CH_2—$ | —CH₂—CH₂—N(CH₃)—CH₂—CH₂— | | $CH_3$ | $CH_3—CH_2$ |

-continued

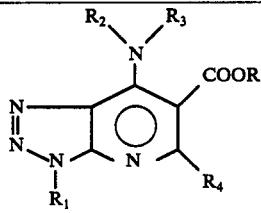

| Example | R₁ | R₂ | R₃ | R₄ | R |
|---------|----|----|----|----|----|
| 49 | H | CH₃CO— | H | H | H |
| 50 | H | CH₃—(CH₂)₃— | H | CH₃ | CH₃—CH₂— |
| 51 | ⌬—CH₂— | CH₃—(CH₂)₃— | H | CH₃ | CH₃—CH₂— |
| 52 | H | CH₃—(CH₂)₃— | H | CH₃ | H |
| 53 | H | CH₃—(CH₂)₃— | H | H | CH₃—CH₂— |
| 54 | H | CH₃—(CH₂)₃— | ⌬ | H | CH₃—CH₂— |
| 55 | H | CH₃—(CH₂)₃— | H | H | H |
| 56 | H | —CH₂—CH₂—CH₂—CH₂—CH₂— | | CH₃ | H |
| 57 | C₂H₅ | —CH—CH—CH—CH₂—CH₂—<br>                 CH₃ | | H | H |

What is claimed is:

1. A compound of the formula

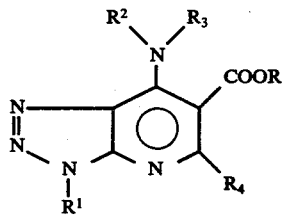

wherein R is hydrogen or lower alkyl; R₁ is hydrogen, lower alkyl, phenyl, benzyl or phenethyl; R₂ and R₃ each is hydrogen, lower alkyl, lower alkenyl, lower alkanoyl, R₅, R₆-phenyl, R₅, R₆-phenyl-lower alkyl, di-lower alkylamino-lower alkyl, R₅, R₆-benzoyl, methanesulfonyl, benzenesulfonyl or toluenesulfonyl; or the group

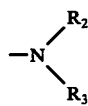

is pyrrolidino, piperidino, 4-lower alkylpiperidino, pyrazolyl, pyrimidino, pyridazino, piperazino or N⁴-lower alkylpiperazino; R₄ is hydrogen, C₁-C₄-lower alkyl or phenyl; R₅ is hydrogen, halogen, lower alkyl, trifluoromethyl, amino or carboxy; R₆ is hydrogen, halogen of lower alkyl; and physiologically acceptable salts thereof.

2. A compound of the formula

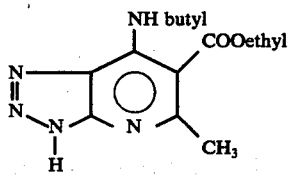

3. A compound as in claim 1 wherein R₃ is hydrogen.

4. A compound as in claim 3 wherein R₂ is lower alkyl.

5. A compound as in claim 1 wherein the group

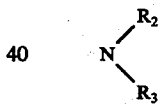

is pyrrolidino, piperidino, 4-lower alkylpiperidino, pyrazolyl, pyrimidino, pyridazino, piperazino or N⁴-lower alkylpiperazino.

6. A compound as in claim 1 wherein the group

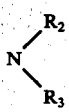

is piperidino or piperazino.

7. A compound as in claim 4 wherein R, R₁, R₂ and R₄ each is lower alkyl and R₃ is hydrogen.

8. A compound as in claim 7 wherein R₄ is methyl.

9. A compound as in claim 4 wherein R, R₁ and R₂ each is ethyl, R₃ is hydrogen and R₄ is methyl.

10. A compound as in claim 4 wherein R is ethyl, R₁ is isobutyl, R₂ is butyl, R₃ is hydrogen and R₄ is methyl.

11. A compound as in claim 4 wherein R and R₁ each is ethyl, R₂ is butyl, R₃ is hydrogen and R₄ is methyl.

* * * * *